(12) United States Patent
Abuto et al.

(10) Patent No.: US 9,237,973 B2
(45) Date of Patent: Jan. 19, 2016

(54) TREATED APERTURES

(75) Inventors: Frank P. Abuto, Johns Creek, GA (US); Marsha R. Forthofer, Woodstock, GA (US); Nicole E. Cieslak, Appleton, WI (US); Donald E. Waldroup, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 261 days.

(21) Appl. No.: 13/362,915

(22) Filed: Jan. 31, 2012

(65) Prior Publication Data

US 2013/0197462 A1   Aug. 1, 2013

(51) Int. Cl.

| A61F 13/15 | (2006.01) |
|---|---|
| A61F 13/511 | (2006.01) |
| A61F 13/512 | (2006.01) |
| A61F 13/513 | (2006.01) |
| A61F 13/537 | (2006.01) |
| A61F 13/51 | (2006.01) |

(52) U.S. Cl.
CPC .............. *A61F 13/511* (2013.01); *A61F 13/512* (2013.01); *A61F 13/51305* (2013.01); *A61F 13/53704* (2013.01); *A61F 2013/51061* (2013.01); *A61F 2013/51066* (2013.01); *A61F 2013/53782* (2013.01)

(58) Field of Classification Search
CPC ............... A61F 13/53704; A61F 13/51305; A61F 13/511; A61F 13/5376; A61F 13/512; A61F 13/53782; A61F 2013/53782; A61F 2013/51061; A61F 2013/51066; A61F 2013/530875

USPC .................................. 604/367, 381, 383, 382
See application file for complete search history.

(56) References Cited

U.S. PATENT DOCUMENTS

| 3,814,101 A | 6/1974 | Kozak |
|---|---|---|
| 3,838,692 A | 10/1974 | Levesque |
| 3,901,238 A | 8/1975 | Gellert |
| 4,062,362 A | 12/1977 | Schaar |
| 4,585,449 A | 4/1986 | Karami |
| 4,629,457 A | 12/1986 | Ness |
| 4,755,413 A | 7/1988 | Morris |
| 4,820,294 A | 4/1989 | Morris |
| 5,188,625 A | 2/1993 | Van Iten |
| 5,431,643 A | 7/1995 | Ouellette |
| 5,620,742 A | 4/1997 | Lauritzen |
| 5,658,639 A | 8/1997 | Curro |
| 5,895,623 A | 4/1999 | Trokhan |
| 5,989,478 A | 11/1999 | Ouellette |
| 6,025,049 A | 2/2000 | Ouellette |
| 6,291,050 B1 | 9/2001 | Cree |
| 6,350,711 B1 | 2/2002 | Potts et al. |
| 6,395,957 B1 | 5/2002 | Chen |

(Continued)

FOREIGN PATENT DOCUMENTS

| EP | 0 272 118 A2 | 6/1988 |
|---|---|---|
| EP | 0 165 807 B1 | 8/1989 |

(Continued)

*Primary Examiner* — Jacqueline Stephens
(74) *Attorney, Agent, or Firm* — Kimberly-Clark Worldwide, Inc.

(57) ABSTRACT

A personal care article comprising a nonwoven fluid permeable topsheet having a body-facing surface and an opposing backside surface, a fluid impermeable backsheet and at least one intermediate layer disposed therebetween, wherein said fluid permeable topsheet comprises apertured holes wherein at least 10% of the aperture holes are treated with a hydrophilic treatment agent.

16 Claims, 3 Drawing Sheets

(56) References Cited

U.S. PATENT DOCUMENTS

| | | |
|---|---|---|
| 6,410,823 B1 | 6/2002 | Daley |
| 6,478,786 B1 | 11/2002 | Glaug |
| 6,649,222 B1 | 11/2003 | D'Agostino |
| 6,685,686 B2 | 2/2004 | Roxendal |
| 7,381,299 B2 | 6/2008 | Shannon |
| 7,771,406 B2 | 8/2010 | Mueller |
| 2002/0143304 A1* | 10/2002 | Elder et al. .................. 604/360 |
| 2002/0193765 A1 | 12/2002 | Kudo |
| 2003/0050618 A1* | 3/2003 | Kondo et al. ................ 604/383 |
| 2003/0124311 A1 | 7/2003 | Cree et al. |
| 2005/0177123 A1* | 8/2005 | Catalan ........................ 604/381 |
| 2006/0184150 A1* | 8/2006 | Noel ............................. 604/383 |
| 2006/0269706 A1 | 11/2006 | Shannon |
| 2007/0005024 A1 | 1/2007 | Weber |
| 2007/0009657 A1 | 1/2007 | Zhang |
| 2007/0135007 A1 | 6/2007 | McCarthy |
| 2007/0141305 A1 | 6/2007 | Kasai |
| 2007/0264437 A1 | 11/2007 | Zimmermann |
| 2007/0298216 A1 | 12/2007 | Jing |
| 2008/0090050 A1 | 4/2008 | Seyler |
| 2009/0076430 A1 | 3/2009 | Simpson |
| 2009/0197071 A1 | 8/2009 | Cramail |
| 2009/0227164 A1 | 9/2009 | Broch-Nielsen |
| 2009/0264836 A1 | 10/2009 | Roe |
| 2009/0264845 A1 | 10/2009 | Himori |
| 2010/0069864 A1 | 3/2010 | Berland |
| 2010/0222757 A1* | 9/2010 | Tee et al. ...................... 604/367 |

FOREIGN PATENT DOCUMENTS

| | | |
|---|---|---|
| EP | 0 594 983 A1 | 5/1994 |
| EP | 0 546 580 B1 | 10/1996 |
| EP | 0 794 280 A2 | 9/1997 |
| EP | 0 985 392 A1 | 3/2000 |
| EP | 0 985 740 A1 | 3/2000 |
| EP | 0 997 576 A2 | 5/2000 |
| EP | 1 856 314 A2 | 11/2007 |
| EP | 1 931 397 B1 | 4/2009 |
| WO | WO 97/40793 A1 | 11/1997 |
| WO | WO 00/14323 A1 | 3/2000 |
| WO | WO 2009/062998 A1 | 5/2009 |
| WO | WO 2009/086347 A1 | 7/2009 |

* cited by examiner

TREATED APERTURES

FIELD OF THE INVENTION

The present invention relates to personal care products, particularly disposable absorbent articles, comprising hydrophilically treated apertured holes that aid in keeping the surface of the article to appear and feel clean.

BACKGROUND OF THE INVENTION

A number of disposable, personal care articles that collect body fluids exist; however, their tendency to leak off the surface before the liquid absorbent capacity is entirely used is an ongoing challenge that faces many manufacturers. Additionally, certain fluids, such as menses and runny BM (feces), have viscoelastic properties that make obtaining good intake and distribution performance particularly problematic. In particular, the relatively high viscosity and/or elasticity of such fluids tend to interfere with the absorption and distribution of the fluids within the absorbent article. In other instances, intake performance of an absorbent article may be impeded when components of the menses block the channels between the particles or fibers contained in the absorbent article. This phenomenon is often referred to as fouling. Although attempts have been made to improve the effects of fouling through modification of the viscoelastic properties of the fluid itself, actual improvement into the absorbent article still needs development.

In addition to problems with leakage in some disposable, personal care articles, there are also hygienic issues that directly affect the user. Often the body fluid sits in direct contact with the user which makes for an unpleasant and unclean feel. Particularly with feminine hygiene products such as sanitary napkins, the unpleasant or unclean feeling, that may often be caused by bodyside liner stains, may lead to poor perception in product performance and the inability to get maximum use from the product.

Therefore, there is a need in the art for a treatment, that may be used in connection with personal care products, such as absorbent articles, that provides improved intake and distribution performance, reduced leakage, reduced stains, reduced surface rewet or flowback for an overall cleaner, drier and more pleasant feel and user experience.

SUMMARY OF THE INVENTION

A personal care article comprising a nonwoven fluid permeable topsheet having a body-facing surface and an opposing backside surface, a fluid impermeable backsheet and at least one intermediate layer disposed therebetween, wherein said fluid permeable topsheet comprises apertured holes wherein at least 10% of the aperture holes are treated with a hydrophilic treatment agent.

BRIEF DESCRIPTION OF THE DRAWINGS

FIG. 1 shows a feminine care absorbent product wherein several layers are shown and wherein the topsheet has hydrophilically treated apertures.

DETAILED DESCRIPTION OF THE INVENTION

While the specification concludes with the claims particularly pointing out and distinctly claiming the invention, it is believed that the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein. Except where specific examples of actual measured values are presented, numerical values referred to herein should be considered to be qualified by the word "about".

As used herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

As used herein, the phrase "absorbent article" generally refers to devices which absorb and contain body fluids, and more specifically, refers to devices which are placed against or near the skin to absorb and contain the various fluids discharged from the body and, in particular, viscoelastic fluids. Examples of absorbent articles include, but are not limited to, absorbent articles intended for personal wear, such as diapers; incontinence products; feminine hygiene products, such as feminine napkins, panty liners, tampons, and interlabial pads; other personal garments; and the like.

As used herein, "fouling" means the change in permeability of a fluid as it passes through a porous medium. More particularly, fouling is the reduction in permeability that occurs when components of a fluid pass through a porous medium and interact with the material structure, decreasing the inherent permeability of the porous material.

The term "hydrophilic", as used herein, refers to surfaces with water contact angles well below 90°.

The term "hydrophobic", as used herein, refers to the property of a surface to repel water with a water contact angle from about 90° to about 120°.

As used herein, "rewetting" refers to the amount of fluid that comes from the absorbent core back into and through the top layer, nonwoven surface. This may also be referred to as "flowback".

The term "superhydrophobic" refers to the property of a surface to repel water very effectively. This property is quantified by a water contact angle generally exceeding 150°.

The present invention relates to improved personal care products, particularly disposable absorbent articles. Personal care products of the present invention include, but are not limited to, feminine hygiene products like sanitary wipes and menses absorbing devices (e.g., sanitary napkins and tampons), infant and child care products such as disposable diapers, absorbent underpants, and training pants, wound dressings such as bandages, incontinent products, products for wiping and absorbing oils, and the like.

Figure 1:
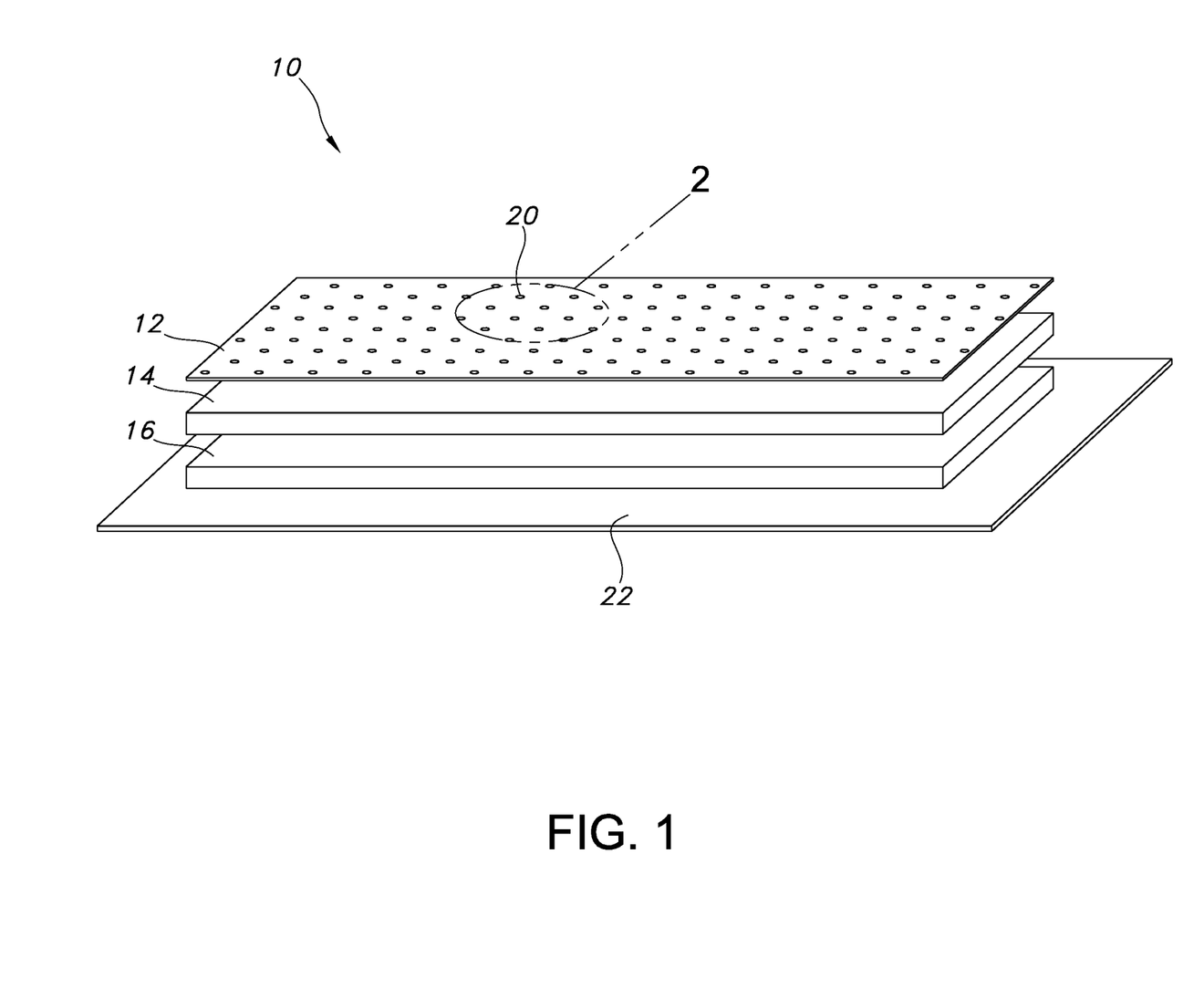
FIG. 1 is an embodiment of a personal care article of the present invention. Specifically.

Disposable absorbent articles (10) such as the feminine care absorbent product, illustrated in FIG. 1, for example, may include a liquid permeable topsheet (12), a substantially liquid impermeable backsheet (22) joined to the topsheet (12), and an absorbent core (16) positioned and held between the topsheet (12) and the backsheet (22). The topsheet (12) is operatively permeable to the liquids that are intended to be held or stored by the absorbent article (10), and the backsheet (22) may be substantially impermeable or otherwise operatively impermeable to the intended liquids. The absorbent article (10) may also include an additional layer(s) (14) such as that shown in FIG. 1. This additional layer(s) (14) may be a liquid intake layer, liquid wicking layers, liquid distribution layers, transfer layers, barrier layers, and the like, as well as combinations thereof. Disposable absorbent articles (10) and the components thereof can operate to provide a body-facing surface (top surface of the topsheet (12)) and a garment-facing surface (back surface of the backsheet (22)). As used herein, the "body-facing" or "bodyside" surface refers to the surface of the topsheet (12) that is disposed toward or placed adjacent to the body of the wearer during ordinary use. The "garment-side surface" refers to the backsheet (22) where the back of the surface is disposed away from the wearer's body and adjacent to the garment of the wearer during ordinary use. Suitable absorbent articles are described in more detail in U.S. Pat. No. 7,632,258.

The fluid permeable topsheet (12) of the present invention may be left untreated or may be treated with a hydrophobic, superhydrophobic composition that helps to keep fluids from sitting atop the surface which can leave an unpleasant and/or unclean feeling from stains, accumulated debris or wetness on the surface. The disposable absorbent articles (10) of the present invention are particularly adapted to receive fluids having viscoelastic properties, such as menses, mucous, blood products, and feces, among others to reduce stain area, reduce rewet, improve fluid intake, distribution, absorption properties and decrease leakage. More importantly, the fluid permeable topsheet (12) is preferably a substantially hydrophobic nonwoven such as spunbond, spunbond-meltblown-spunbond (SMS), Bonded Carded Web (BCW), spunlace or coform comprising apertured holes (20) wherein the apertured holes (20) are treated with a hydrophilic treatment agent, said treatment agent increasing the surface energy in and around the aperture holes to preferentially channel fluid flow into the holes (20) to provide advantages of the present invention in protecting against stains, re-wetting, particulate debris accumulation on the body-facing surface and other unpleasantries.

Although the present disclosure is discussed primarily in combination with feminine hygiene products such as feminine napkins, panty liners, and interlabial pads, it will be readily apparent to one skilled in the art based on the disclosure that the products and methods described herein can also be used in combination with numerous other absorbent articles designed to absorb fluids other than menses such as runny BM, urine and the like.

Fluid Permeable Topsheet

The absorbent articles (10) of the present invention comprise a fluid permeable topsheet (12) that is preferably a nonwoven, body-facing fibrous sheet material. The present invention provides an advantage over topsheets comprising a thermoplastic film since nonwovens are generally softer, cause less sweating and irritation from sweat, and avoids the plastic feel or rustling that is often associated with plastics and films. Nonwovens of the present invention include, but are not limited to, spunbond, meltblown, coform, air-laid, bonded-carded web materials, hydroentangled (spunlace) materials, combinations thereof and the like. For example, the fibers from which the nonwoven material is made may be produced by the meltblowing or spunbonding processes, including those producing bicomponent, biconstituent or polymer blend fibers which are well known in the art. These processes generally use an extruder to supply melted thermoplastic polymer to a spinneret where the polymer is fiberized to yield fibers which may be staple length or longer. The fibers are then drawn, usually pneumatically, and deposited on a moving formations mat or belt to form the nonwoven fabric. The fibers produced in the spunbond and meltblown processes may be microfibers. Microfibers of the present invention are small diameter fibers having an average diameter not greater than about 75 microns, for example, having an average diameter of from about 0.5 microns to about 50 microns, or more particularly, microfibers may have an average diameter of from about 2 microns to about 40 microns.

Spunbond nonwoven fabrics are generally bonded in some manner as they are produced in order to give them sufficient structural integrity to withstand the rigors of further processing into a finished product. Bonding can be accomplished in a number of ways such as hydroentanglement, needling, ultrasonic bonding, adhesive bonding, stitchbonding, through-air bonding and thermal bonding.

The nonwoven also may be a bonded carded web. Bonded carded webs are made from staple fibers, which are usually purchased in bales. The bales are placed in a picker, which separates the fibers. Then, the fibers are sent through a combing or carding unit, which further breaks apart and aligns the staple fibers in the machine direction to form a generally machine direction-oriented fibrous nonwoven web. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable bonding method, particularly when using bicomponent staple fibers, is through-air bonding.

The nonwoven may also be produced through airlaying. The production of airlaid nonwovens is well defined in the literature and documented in the art. Examples include the DanWeb process as described in U.S. Pat. No. 4,640,810 to Laursen et al., the Kroyer process as described in U.S. Pat. No. 4,494,278 to Kroyer et al., U.S. Pat. No. 5,527,171 to Soerensen, and the method of U.S. Pat. No. 4,375,448 to Appel et al., or other similar methods.

The nonwoven of the present invention may also be a multilayer laminate. An example of a multilayer laminate is an embodiment wherein some of the layers are spunbond and some meltblown such as a spunbond/meltblown/spunbond (SMS) laminate as disclosed in U.S. Pat. No. 4,041,203 to Brock et al., U.S. Pat. No. 5,169,706 to Collier, et al, and U.S. Pat. No. 4,374,888 to Bornslaeger. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 OSY (ounces per square yard) (6 to 400 gsm), or more particularly from about 0.75 to about 3 OSY.

Hydrophobic/Superhydrophobic Coating

Figure 2:
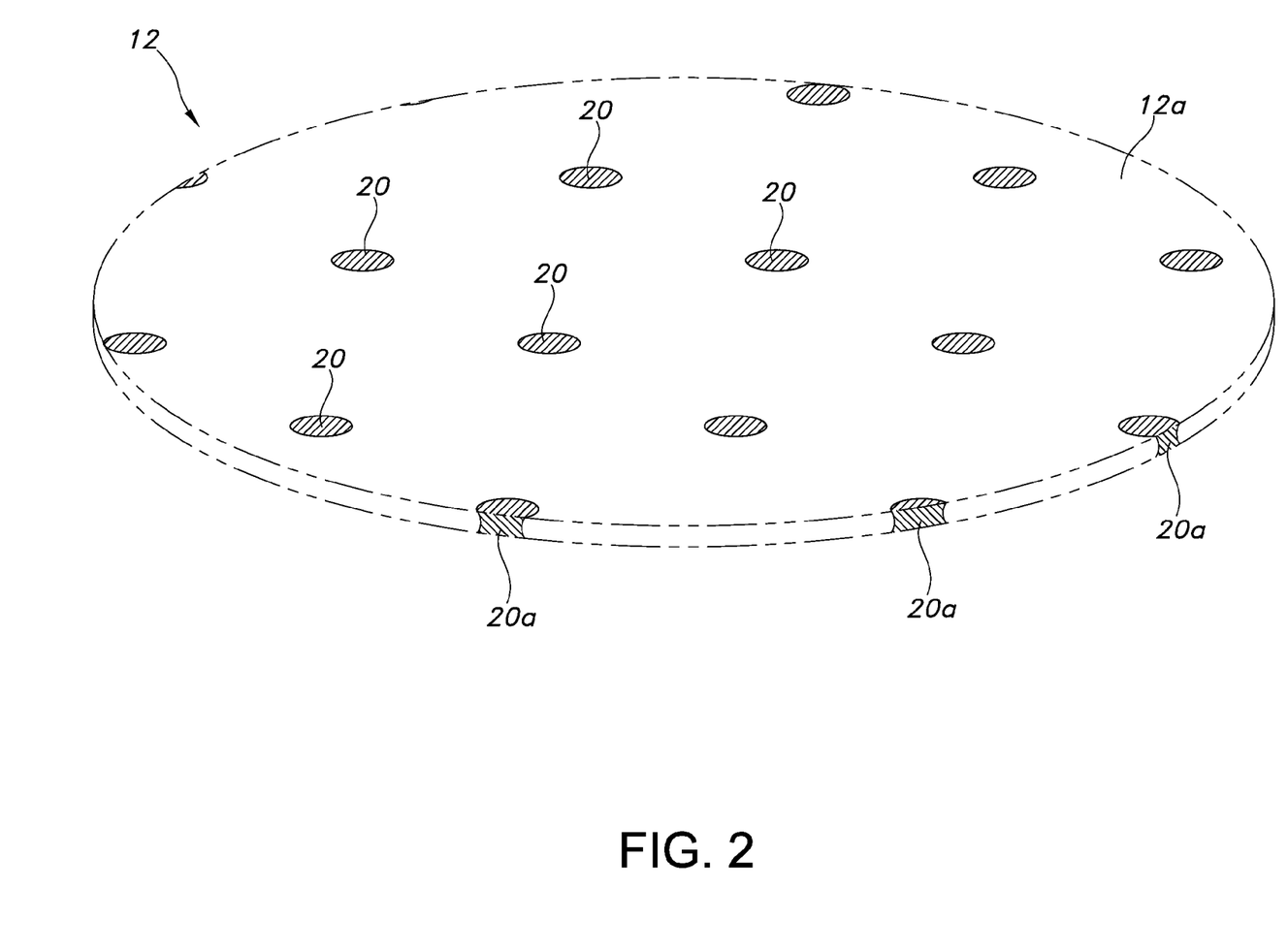
FIG. 2 shows a top and cross-cut view of the hydrophobic treated topsheet of the present invention with hydrophilically treated apertures.
Figure 3:
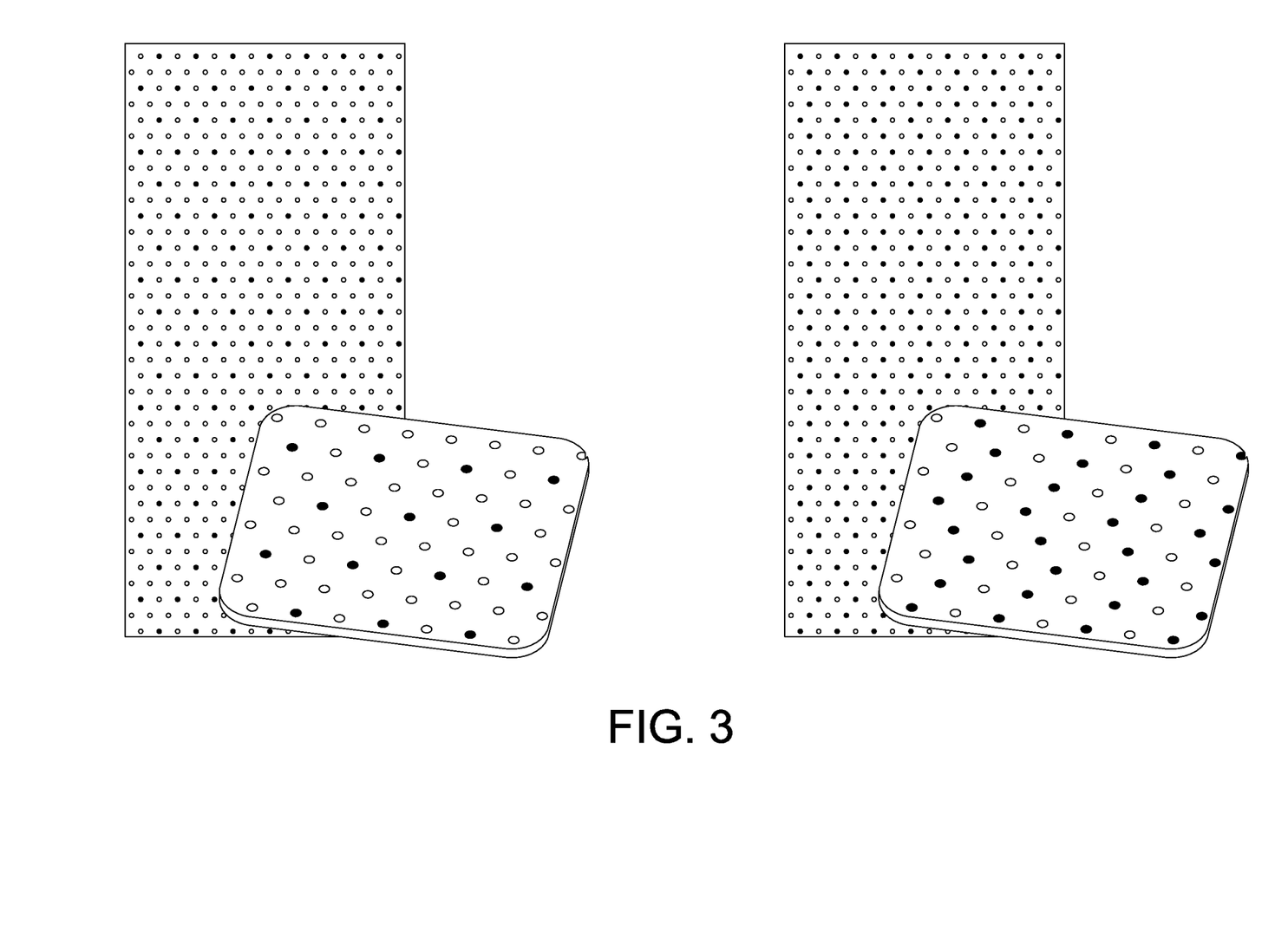
FIG. 3 shows two embodiments of the present invention showing that the apertures may be treated as patterns, wherein, for example 25% of the apertures may be treated in a "diamond" pattern (left) or wherein, for example, 50% of the apertures may be treated in a "zig-zag" pattern (right).

The nonwoven material of the present invention may or may not be treated with a hydrophobic or a superhydrophobic composition. If treated, as shown in FIG. 2, a major portion of the surface (12a) of the nonwoven topsheet (12) may be treated with a surface composition selected from a hydrophobic composition, a superhydrophobic composition, or combinations thereof. The other portion of the surface (12a) will comprise of hydrophilic treated (20a) apertures (20) as will be subsequently detailed.

The hydrophobic coating may be a hydrophobic polymer that is dispersible in water including, but not limited to, fluorinated or perfluorinated polymers. The fluorinated or perfluorinated polymer may need to be modified by introducing a comonomer onto their molecular structure. Suitable comonomers include, but are not limited to, ethylenically unsaturated monomers comprising functional groups which are capable of being ionized in water. One example is ethylenically unsaturated carboxylic acid, such as acrylic acid. One example of a hydrophobic composition is a commercially available modified perfluorinated polymer compound available from DuPont® as a water-based product under the trade name Capstone® ST-100. Another example of a hydrophobic composition that may be used to coat the surface of the nonwoven of the present invention is commercially available from Aculon® Company of San Diego, Calif., U.S.A. as H1-F® proprietary composition.

In addition to the above examples, other hydrophobic materials suitable for the present invention are well defined and documented in the art. For example, US patent application 2002/0064639 describes hydrophobic compositions selected from the group consisting of silicones, fluorochemicals, zirconium compounds, oils, latexes, waxes, crosslinking resins, and blends thereof. Representative water repellent fluorochemical compounds described in U.S. Pat. No. 7,407,899 include fluorochemical urethanes, ureas, esters, ethers, alcohols, epoxides, allophanates, amides, amines (and salts thereof), acids (and salts thereof), carbodiimides, guanidines, oxazolidinones, isocyanurates, and biurets. U.S. Pat. No. 6,548,732 describes hydrophobic substances from the group consisting of theobroma oil, cacao butter, cocoa butter, petrolatum, mineral jelly, white mineral oil, dimethicone, zinc oxide preparation, chinese white, zinc white, beeswax, lanolin, jojoba oil and combinations thereof. Additionally, U.S. application Ser. No. 13/193,065, filed Jul. 28, 2011 discusses substrates that exhibit superhydrophobic properties when treated with a composition comprising a hydrophobic component selected from fluorinated polymers, perfluorinated polymers, and mixtures thereof; nano-structured particles selected from fumed silica, hydrophobic titania, zinc oxide, nanoclay, and mixtures thereof; and water for an overall water-based, non-organic solvent. Examples of such compositions and surfaces in U.S. application Ser. No. 13/193,065, filed Jul. 28, 2011 exemplify the superhydrophobic treated surfaces that may be used as the nonwoven topsheet of the present invention.

The present invention presents both hydrophobic and superhydrophobic coated nonwovens to aid in reducing the presence of body fluids on the body-facing surface of the topsheet (12) making it more likely for the body fluid to gravitate towards the hydrophilic apertures (20) and into the absorbent core (16).

Superhydrophobic surface topsheets are those with water contact angles of 150° or greater which, may be achieved, for example, by altering the topography of the surface such as through elevations and depressions to create a rough surface and then applying hydrophobic composition(s) thereto. U.S. Pat. No. 6,800,354, for example, describes a coating having a "nanoscale" structured surface such as by metal oxide particles with a suitable hydrophobic layer disposed on the structured substrate surface. Various other techniques for rendering surfaces superhydrophobic are also documented in, for example, US Patent Application 20090298369. These techniques include roughening hydrophobic polymers such as fluorinated polymers, polydimethylsiloxane, paraffinic hydrocarbons and the like via templating methods, electrospinning to yield small fiber diameters, controlling crystallization, and such. Alternatively, a rough surface can be made by other techniques such as etching, lithography, sol-gel processing, layer-by-layer assembly and the like and the surface modified with a low surface energy material like those hydrophobic materials mentioned previously. Another approach to achieve superhydrophobic properties is to coat a surface with a liquid dispersion that contains at least one low-surface energy component, such as a perfluorinated polymer, in combination with roughening features such as micro and nano structure forming particles that impart surface roughness when the coating composition is sprayed, padded or applied through other common application techniques.

Apertured Topsheet

The nonwoven topsheet (12) of the present invention comprises treated apertured holes (20)/(20a) for attracting body fluids from the body-facing surface and into the absorbent core (16). The apertures (20) may be uniform in size or may be tapered or conical in shape, having a larger opening near the top and a smaller opening near the bottom. Larger opening geometric shapes may be, but are not limited to, circles, triangles, pentagons, ovals, symmetrical, non-symmetrical and the like. The apertures (20) may also be patterned to show various designs or create advantaged depositions of the holes in particular articles in order to minimize re-wetting and/or stains. At least a portion of the apertures (20) will be treated with a hydrophilic treatment agent. Thus, at least about 10%, at least about 25%, at least about 50%, at least about 75% or 100% of the apertures within the nonwoven may comprise a hydrophilic treatment. The apertures may be treated and untreated in a pattern as a design for aesthetically pleasing visual cues, or for functional advantages to minimize re-wetting and/or staining in particular areas of the nonwoven or for a combination of both aesthetic and functional features. Aperture diameters measured on the garment facing surface of the topsheet may range from about 0.1 mm to about 5 mm, from about 0.4 mm to about 1.5 mm or from about 0.5 to about 1.0 mm. The aperture density may also range from about $7.8 \times 10^3$ holes/m$^2$ to about $1.9 \times 10^6$ holes/m$^2$, from about $4.7 \times 10^4$ holes/m$^2$ to about $9.3 \times 10^5$ holes/m$^2$ or from about $1.6 \times 10^5$ holes/m$^2$ to about $3.1 \times 10^5$ holes/m$^2$. The apertures may extend through the topsheet (12) thickness from the body-facing surface through and to the backside of the topsheet (12); though in some instances such as with a multi-layered laminate topsheet (not shown), the apertures (20) may advantageously extend from the body-facing surface through to one or more layers (not shown) but not completely through to the backside of the laminated topsheet (not shown).

Hydrophilic Treatment of Apertures

The entirety of apertures of the present invention may be treated with a hydrophilic treatment agent. If not all of the apertures are treated, at least from about 10%, at least from about 25% at least from about 50%, or at least from about 75% of the apertures are treated with a "hydrophilic treatment agent" (20a) that increases the capillary action of the fluid and assures that the liquid flows preferentially through the apertures (20) in the nonwoven topsheet (12) and into the absorbent core (16). Additionally, the re-wetting is significantly decreased and the staining is significantly minimized. Thus, the present invention leaves the consumer with a product that feels more dry and clean for an overall improved performing product.

Fluids having viscoelastic properties, such as menses, mucous, blood products, feces and other body fluids for which personal care products are used have a tendency to interfere with the absorption and distribution properties of the personal care products. Thus, the treated (20a) apertures (20) of the present invention provide an advantage not only in drawing the fluids through capillary action but also in reducing the viscosity and elasticity of viscoelastic fluids thus enabling the fluid to flow more easily through the topsheet (12) into the absorbent core (16). Additionally, the fouling effects of the fluids are also reduced due to reduced viscosity and or elasticity, particularly of menses fluid.

The hydrophilic treatment agents described herein may exert various combinations of effects on viscosity, elasticity, and fouling, depending on the concentration and deposition at which they are applied to the substrate. The hydrophilic treatment agent of the present invention may be selected from the group consisting of polyethylene glycol laurates, polyethylene glycol lauryl ethers, and combinations thereof. Advantageously, the polyethylene glycol laurates and polyethylene glycol lauryl ethers are capable of reducing both the viscosity and elasticity of viscoelastic fluid. Examples of suitable polyethylene glycol laurates include, but are not limited to, polyethylene glycol 400 monolaurate, polyethylene glycol 600 monolaurate, polyethylene glycol 1000 monolaurate, polyethylene glycol 4000 monolaurate, polyethylene glycol 600 dilaurate, and combinations thereof. Examples of suitable polyethylene glycol lauryl ethers include, but are not limited to, polyethylene glycol 600 lauryl ether. Notably, the polyethylene glycol lauryl ether and/or polyethylene glycol laurate serves not only as a hydrophilic treatment agent, but is further capable of reducing the fouling properties of viscoelastic fluid. Such hydrophilic treatment agents include, but are not limited to, polyethylene glycol (PEG) 600 lauryl ether and related compounds, polyethylene glycol (PEG) 600 monolaurate and related compounds, and combinations thereof.

In addition to the PEG laurates and PEG lauryl ethers, other polyethylene glycol derivatives may be viscoelastic agents (i.e., are capable of reducing the viscosity and elasticity of viscoelastic fluids) and may be used as hydrophilic treatment agents for the personal care products described herein. As used herein, the term "polyethylene glycol derivative" includes any compound comprising a polyethylene glycol moiety. Examples of other suitable PEG derivatives include, but are not limited to, PEG monostearates such as PEG 200 monostearates and PEG 4000 monostearate; PEG dioleates such as PEG 600 dioleate and PEG 1540 dioleate; PEG monooleates such as PEG 600 monooleate and PEG 1540 monooleate; PEG monoisostearates such as PEG 200 monoisostearate; and PEG 16 octyl phenyl. Particular polyethylene glycol derivatives for use as hydrophilic treatment agents are those that improve intake time of viscoelastic fluids as well as reduce viscosity and elasticity. Examples of such include, but are not limited to, PEG derivatives include PEG 1540 dioleate, PEG 600 monooleate, PEG 1540 monooleate, and PEG 16 octyl phenyl. These PEG derivatives may be used alone or in combination with PEG 600 monolaurate, PEG 600 lauryl ether, and/or other viscoelastic agents as a hydrophilic treatment agent.

In certain embodiments, the hydrophilic treatment agents described herein, such as polyethylene glycol 600 lauryl ether and/or the polyethylene glycol 600 monolaurate, may be used in combination with each other or in combination with other viscoelastant agents. Examples of additional viscoelastant agents that may be used in combination with the hydrophilic treatment agents include, but are not limited to, sodium citrate, dextran, cysteine, Glucopon 220UP (available as a 60% (by weight) solution of alkyl polyglycoside in water from Henkel Corporation), Glucopon 425, Glucopon 600, Glucopon 625. Other suitable viscoelastant agents are described in U.S. Pat. No. 6,060,636. Surprisingly, it has been discovered that certain viscoelastant agents that actually increase the fouling effect of viscoelastic fluids when used alone, will in fact improve fouling effects when used in combination with PEG 600 lauryl ether and/or PEG 600 monolaurate. For example, in one embodiment, sodium citrate may be used in combination with PEG 600 monolaurate as a hydrophilic treatment agent. When two or more hydrophilic treatment agents are used in combination, the proportion of each hydrophilic treatment agent applied to the personal care product is preferably in a ratio of from about 1:2 to about 2:1, and more preferably is about 1:1.

The hydrophilic treatment agent may be applied in varying amounts depending on the desired results and application. Typically, hydrophilic the treatment agent is applied to the apertures in an amount of from about 0.1% to about 40%, from about 0.1% to about 20%, or from about 3% to about 12%, by weight of the treated substrate.

In addition to the amount of hydrophilic treatment agent used within the apertures (20), the size of the apertures, the distance from each other on the substrate or the density of the holes/% open area play a significant role in contributing to the advantages of the present invention. For example, aperture holes that are too large, (while advantageous in allowing fluid to more easily enter the absorbent system) may be disadvantageous in contributing to increased rewet during product use such as when the wearer applies pressure to the product, for example in a sitting position. On the other hand, very small aperture holes in combination with low hole density, (low % open area) (while advantageous for minimizing rewet) may be disadvantageous for fast fluid intake; and for menses in particular, may result in higher accumulation of debris and particulate matter on the topsheet. This may lead to the plugging of apertures resulting in a wetter, unclean product. Hydrophilic treatment agents, such as polyethylene glycol (PEG) 600 lauryl ether, applied into (20a) of the apertures (20) help to breakdown the menses by reducing its viscosity and elasticity, improve intake and reduce debris accumulation on the topsheet surface. Inventors have found that about 1 wt. % to about 10 wt. % of such treatments applied in the apertures having a size range of from about 0.1 mm to about 5 mm, from about 0.4 mm to about 1.5 mm or from about 0.5 to about 1.0 mm and a hole density range of about $7.8 \times 10^3$ holes/m$^2$ to about $1.9 \times 10^6$ holes/m$^2$, from about $4.7 \times 10^4$ holes/m$^2$ to about $9.3 \times 10^5$ holes/m$^2$ or from about $1.6 \times 10^5$ holes/m$^2$ to about $3.1 \times 10^5$ holes/m$^2$, in a hydrophobic coated (12a) topsheet (12), the resulting disposable absorbent article (10) provides the desired balance of fluid intake, reduced debris accumulation and rewet for improved pad cleanliness and user experience.

Hydrophobic/Hydrophilic Treatments for One-Way Valve

The present invention strategically combines hydrophilic and hydrophobic compositions to treat a nonwoven topsheet (12) in order to significantly reduce re-wetting and staining that often occurs during the use of personal care products such as disposable absorbent articles (10). The aperture treated topsheet (12) functions as a 'one-way valve' that allows fluid to more easily migrate from the body-facing surface to the absorbent core (16). Due to the design and composition utilized in the present invention, there is less undesirable rewetting or flowback caused by the fluid re-entering from the absorbent core (16) to the body-facing surface of the topsheet (12). One way to achieve a 'one-way valve' in the nonwoven topsheet (12) of the present invention is by aperture hole design, such as a conical hole design with a wider diameter hole on the body-facing side of the topsheet (12) than on the opposing back side of the topsheet (12) in combination with strategic hydrophilic and hydrophobic treatments. The aperture hole (20) is treated (20a) with a hydrophilic treatment agent while either or both of the body-facing surface of the topsheet (12) and the back side of the topsheet (12) are treated with a hydrophobic or a superhydrophobic composition. Utilization of a "one way valve" system drives the fluid into the absorbent layer (16), away from the consumer's body such that the consumer feels more dry and clean for an overall improved performing product.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

A 4" by 8" rectangular piece of apertured spunbond nonwoven topsheet material with a basis weight of 0.50 OSY (ounces per square yard), aperture hole diameters of about 1-2 mm, hole density of about 28.5 holes/in$^2$ ($4.4 \times 10^4$ holes/m$^2$) and about 5 mm spacing between the holes was treated all over the body-side surface with Lutensol A65N hydrophilic treatment agent commercially available from the BASF® corporation. The treatment agent was applied to the material surface using a Paramaco Quick Change Complete Handproofer with Evenflow Mechanical Anilox 220P engraved roller available from Parmaco® Global. About 1 mL of the Lutensol A65N was applied to the hand proofer via an eye dropper and applied to the surface of the spunbond substrate per manufacturer's directions. The treatment add-on amount was recorded as weight percent (% wt.) of the original spunbond substrate sample weight; and the treated sample was stored in a sealed plastic bag prior to testing with menses simulant.

The treated spunbond topsheet was then tested for fluid intake, rewet and stain-size using menses simulant, as described in U.S. Pat. No. 5,883,231. (Menses simulant available from Cocalico Biological®, Reamstown, Pa.) consisting of 70% processed swine blood and 30% gentamicin (egg whites). The test apparatus set-up comprised model 55-4143 Harvard (Southwick, Mass.) Pump resting on a VWR Scientific model 100 rocking platform, a 5/8" diameter steel ball inside a 60 mL Slip Top Syringe manufactured by BD, Franklin Lakes N.J., a hypodermic needle attached to the syringe via Tygon R-3606 1/16" ID 1/8" OD tubing available from VWR scientific and a clamping stand. The top-sheet was tested over a simulated feminine pad comprising the fluid permeable apertured topsheet, fluid impermeable polyethylene (plastic) backsheet and intermediary intake and absorbent core layers disposed therebetween.

The intake layer, adjacent to the topsheet, was a 125 gsm, 2.08 mm thick airlaid nonwoven material manufactured with 81%/19% pulp/binder fiber ratio—(Koch 4825 FiberVision ECS806), 0.06 g/cc density. The absorbent layer, disposed between the intake layer and backsheet was a 240 gsm, 0.17 g/cc density airlaid material manufactured with 67%/8% pulp/binder fiber ratio and 25% super absorbent particles.

Approximately 30 mL of menses simulant was pulled into the syringe that was mounted onto the rocking platform to allow proper and continuous mixing by the steel ball therein. The needle was positioned vertically approximately 2-3 mm above the simulated pad surface by clamping it to the stand and the pump started to deliver 4 mL of the menses simulant to the pad surface at a rate of 4 mL/min. The intake time was recorded as the time from the first drop of simulant contacted the pad to when the no more absorption on the surface was visible.

After weighing, the sample was photographed in a controlled lighting environment with a Sony 3CCD Color Video Camera with a Sony VCL 707BXM lens. This image was analyzed using the ImageJ software, a public domain image processing software developed by the National Institute of Health and available for download from NIH.gov. Adjusting of the color threshold along with calibration of the image allowed for an approximate area of the surface stain to be determined.

Rewet Test:

After imaging, the sample was tested for rewet. Rewet test is used to determine the amount of fluid that will come back to the surface when a load is applied. The amount of fluid that comes back through the surface is called "rewet value". The more the fluid that comes through the surface, the larger the rewet value. Lower rewet values are associated with a drier material and, thus, a drier product. The rewet test was conducted and the values determined as described in U.S. Pat. No. 7,943,813, except that the rewet tester used a bag of air instead of a bag of water and two pieces of 3" by 5" blotter paper were used instead of one. The blotter papers were weighed and the weight recorded. The sample was placed on the center of the bag in the rewet unit and the blotter papers placed on top of the sample. The unit was started to inflate the bag and to apply 1 psi pressure to the sample and blotter paper for 3 minutes. After 3 minutes, the blotter papers were reweighed and the amounts of fluid picked-up by the blotter papers were calculated to determine rewet values.

Three samples were prepared with these specifications and the results recorded in Table 1.

TABLE 1

| Sample | Hydrophilic treatment agent Wt % | Intake Time (sec) | Surface Stain Size (in$^2$) | Rewet Wt (g) |
|---|---|---|---|---|
| 1a | 3.0 | 69 | 0.45 | 0.342 |
| 1b | 2.6 | 70 | 0.43 | 0.345 |
| 1c | 3.0 | 70 | 0.37 | 0.434 |
| Example 1 Average | **** | 70 | 0.42 | 0.374 |

Example 2

In example 2, the test preparation and testing was conducted as in Example 1 except that the hydrophilic treatment agent was Inoterra DWE®, available from the BASF® Corporation. Four samples were prepared with these specifications and the results recorded in the Table 2.

TABLE 2

| Sample | % Hydrophilic treatment agent (Inoterra DWE) | Intake Time (sec) | Surface Stain Size (in²) | Rewet Wt (g) |
|---|---|---|---|---|
| 2a | 2.9 | 67 | 0.49 | 0.560 |
| 2b | 2.9 | 72 | 0.42 | no data |
| 2c | 3.8 | 70 | 0.47 | 0.468 |
| 2d | 3.8 | 70 | 0.45 | 0.524 |
| Average | **** | 70 | 0.46 | 0.517 |

Example 3

In example 3, the test preparation and testing was conducted as in Example 1 except that the Lutesol A65N hydrophilic treatment agent was applied only in the apertures using Artist's Loft synthetic fiber paintbrushes (sizes 0 and 1, available from Michael's stores) rather than all over the sample surface. The hydrophilic treatment agent was applied into approximately 25% of the available apertures in a diamond pattern by dipping the brush tip into the aperture on the material. The results, in Table 3, show that the surface stain area in this example was reduced by about 60% compared to the average stain area of example 1.

TABLE 3

| Example | % Hydrophilic chemistry added | Intake Time (sec) | Surface Stain Size (in²) | Rewet Wt (g) |
|---|---|---|---|---|
| 3 | 0.9 | 94 | 0.16 | no data |
| 4 | 3.2 | 100 | 0.21 | 0.403 |
| 5 | 3.6 | 100 | 0.16 | 0.576 |

Example 4

In example 4, the test preparation and testing was conducted as in Example 3 except that the Lutesol A65N hydrophilic treatment agent was applied in about 50% of the available apertures in a zigzag pattern. The results, compiled in Table 3, show that the surface stain area in this example is reduced by about 50% compared to the average stain area of example 1.

Example 5

In example 5, the test preparation and testing was conducted as in Example 3 except that Lutesol A65N hydrophilic treatment agent was applied in about 100% of the available apertures. The results, compiled in Table 3, show that the surface stain area in this example is reduced by about 60% compared to the average stain area of example 1.

Example 6

In example 6, the test preparation and testing was conducted as in Example 3 except that the hydrophilic treatment agent was Inoterra DWE available from BASF. The results, compiled in Table 4, show that the surface stain area is reduced by about 40% and rewet amount by about 70% compared to the average stain area of example 2.

TABLE 4

| Example | Wt % Hydrophilic treatment agent | Intake Time (sec) | Surface Stain Area (in²) | Rewet Wt (g) |
|---|---|---|---|---|
| 6 | 3.4 | 80 | 0.28 | 0.159 |
| 7 | no data | 90 | 0.12 | 0.035 |
| 8 | 1.8 | 90 | 0.20 | 0.042 |

Example 7

Example 7 is the same as Example 4 except that the hydrophilic treatment agent applied to the 50% of the apertures was Inoterra DWE available from BASF®. The results, in Table 4, show that the surface stain area is reduced by about 70% and the rewet amount by about 90% compared to the average stain area of example 2.

Example 8

Example 8 is the same as example 5, except that hydrophilic treatment agent applied to 100% of the apertures was Inoterra DWE available from BASF. The results are compiled in Table 4. The surface stain size in this example was reduced by about 55% and the rewet weight was reduced by about 90% when compared to the respective average stain area of example 2.

Example 9

Example 9 is the same as example 3 except that Unidyne TG-KC03 hydrophobic composition available from Daikin America was first applied to the all over the sample surface then the hydrophilic treatment agent, Lutensol A65N, available from BASF was applied to treat 25% of the total apertures. The hydrophobic composition was applied using hand proofer, the same as example 3 except that, due to the lower apparent viscosity of the fluid, the hand proofer was used to coat the surface two consecutive times by reapplying the composition to the hand proofer as needed. The hydrophobic composition coated sample was hung in an oven set at 120° Centigrade temperature for one minute to cure the composition then the hydrophilic treatment agent was applied to 25% of the apertures. The coating add-on amounts were recorded as weight percent (wt. %) hydrophobic and hydrophilic of the original sample weight. The results, compiled in Table 5, show about 40% reduction in rewet weight compared to example 1.

TABLE 5

| Example | % hydrophobic chemistry added | % Hydrophilic chemistry added | Intake Time (sec) | Surface Stain Size (in²) | Rewet Wt (g) |
|---|---|---|---|---|---|
| 9 | 5.1 | 1.2 | 120 | 0.46 | 0.213 |
| 10 | 4.1 | 1.6 | 270 | 0.69 | 0.309 |
| 11 | 2.8 | 1.8 | 390 | 0.46 | 0.241 |

Example 10

Example 10 is the same as example 9 except that the hydrophilic treatment agent, Lutensol A65N, available from BASF® was applied to treat 50% of the total apertures in a zigzag pattern similar to example 4. The results in Table 5 show that the rewet weight was reduced by about 20% compared to the Example 1 average.

Example 11

Example 11 is the same as example 10 except that the hydrophilic treatment agent, Lutensol A65N, available from BASF was applied to treat 100% of the total apertures instead of 50%. The results in Table 5 show that the rewet weight was reduced by about 35% compared to the Example 1 average.

Example 12

Example 12 is the same as example 9 except that the hydrophilic treatment agent, Inoterra DWE, available from BASF® was applied to treat 25%. The results in Table 6 show that the rewet weight was reduced by about 55% compared to the Example 2 average.

TABLE 6

| Example | % hydrophobic chemistry added | % Hydrophilic chemistry added | Intake Time (sec) | Surface Stain Size (in$^2$) | Rewet Wt. (g) |
|---|---|---|---|---|---|
| 12 | 5.1 | 1.2 | 180 | 0.42 | 0.224 |
| 13 | 4.6 | no data | 160 | 0.42 | 0.027 |
| 14 | 7.2 | 2.9 | 90 | 0.25 | 0.033 |

Example 13

Example 13 is the same as example 10 except that the hydrophilic treatment agent, Inoterra DWE®, available from BASF® was applied to treat 50% of total apertures. The results in Table 6 show that the rewet weight was reduced by about 90% compared to the Example 2 average.

Example 14

Example 14 is the same as example 11 except that the hydrophilic treatment agent, Inoterra DWE, available from BASF was applied to treat 100% of the total apertures. The results in Table 6 show that the stain area was reduced by about 45% and rewet weight by about 90% compared to the Example 2 average.

Example 15

Example 15 is the same as example 5 except prior to treating 100% of the available apertures with the Lutensol A65N hydrophilic treatment agent from BASF®, a hydrophobic coating composition, Greenshield C6X®, available from BigSky Technologies LLC was applied to the sample as in example 9. The results in Table 7 show that the rewet weight was reduced by about 35% compared to the Example 1 average.

TABLE 7

| Example: | % hydrophobic chemistry added | % Hydrophilic chemistry added | Intake Time (sec) | Surface Stain Size (in$^2$) | Rewet Wt (g) |
|---|---|---|---|---|---|
| 17 | 9.6 | 2.3 | 300 | 0.42 | 0.341 |

Example 16

Example 16 is the same as example 9 except that the hydrophobic composition was Greenshield C6X®, available from BigSky Technologies LLC and the hydrophilic treatment agent, Inoterra DWE®, available from BASF® was applied to treat 25% of the total apertures. Results in Table 8 show minimal to no reduction in stain area or rewet weight compared to example 2 averages.

TABLE 8

| Example: | % hydrophobic chemistry added | % Hydrophilic chemistry added | Intake Time (sec) | Surface Stain Size (in$^2$) | Rewet Wt (g) |
|---|---|---|---|---|---|
| 18 | 6.1 | 1.3 | 360 | .52 | 0.507 |
| 19 | 0.4 | 0.7 | 160 | .44 | 0.025 |
| 20 | 2.5 | 2.9 | 80 | .39 | 0.039 |

Example 17

Example 17 is the same as example 4, except that a hydrophobic coating composition, Greenshield C6X®, available from BigSky Technologies LLC was applied to the sample as in example 9 prior to applying Inoterra DWE® hydrophilic treatment agent to 50% of the apertures. The results in Table 8 show a minor reduction in surface stain area and about 95% reduction in rewet weight compared to the Example 2 average.

Example 18

Example 18 is the same as example 15 except that Inoterra DWE® hydrophilic treatment agent was applied to 100% of the apertures. The results in Table 8 show about 15% reduction in surface stain area and about 90% reduction in rewet weight compared to Example 2 average.

Example 19

Example 19 is similar to example 9 except that Aculon H1-F® hydrophobic composition, manufactured by Aculon®, Inc. of San Diego, Calif. was applied to the test sample using a painter's foam brush available from Michael's® stores by simply painting the hydrophobic composition onto the sample surface. The sample was then air dried at room temperature for at least 10 minutes and Lutensol A 65N hydrophilic treatment agent applied in about 25% of the apertures as in Example 3. The hydrophobic and hydrophilic treatment agent add-on weights were recorded as weight percent (wt. %) of the original sample weight. Results in Table 9 show about 60% reduction in rewet weight compared to Example 1 average.

Example 20

Example 20 is the same as example 4 except prior to the application of the Lutensol A65N hydrophilic treatment agent in 50% of the apertures, a coating of Aculon H1-F hydrophobic composition was applied to sample as in Example 19. The results in the Table 9 show about 10% reduction in surface stain area compared to Example 1 average.

Example 21

Example 21 is the same as example 5 except prior to the application of the Lutensol A65N hydrophilic treatment agent in 100% of the apertures, a coating of Aculon H1-F hydrophobic composition was applied to the sample as in example 19. The results in the Table 9 show about 80% reduction in surface stain area and about 35% in rewet weight compared to example 1 average.

TABLE 9

| Example | % hydrophobic chemistry added | % Hydrophilic chemistry added | Intake Time (sec) | Surface Stain Size (in$^2$) | Rewet Wt (g) |
|---------|------|------|-----|------|-------|
| 21 | 1.9 | 9.8 | 240 | 0.57 | 0.142 |
| 22 | 10.7 | 1.7 | 180 | 0.37 | 0.378 |
| 23 | 9.4 | 1.2 | 150 | 0.09 | 0.245 |

Example 22

Example 22 is the same as example 19, except that Inoterra DWE® hydrophilic treatment agent was used to treat 25% of the apertures. The results, in Table 10, show about 60% reduction in rewet weight compared to example 2 average.

TABLE 10

| Example | % hydrophobic chemistry added | % Hydrophilic chemistry added | Intake Time (sec) | Surface Stain Size (in2) | Rewet Wt (g) |
|---------|------|------|-----|------|-------|
| 24 | 10.6 | 7.5 | 420 | 0.43 | 0.213 |
| 25 | 8.7 | 1.3 | 150 | 0.26 | 0.013 |
| 26 | 11.7 | 1.9 | 150 | 0.11 | 0.041 |

Example 23

Example 23 is the same as example 20, except that Inoterra DWE® hydrophilic treatment agent was used to treat 50% of the apertures. The results, in Table 10, show about 45% reduction in surface stain area and about 95% reduction in rewet weight compared to Example 2 average.

Example 24

Example 24 is the same as example 21, except that Inoterra DWE® hydrophilic treatment agent was used to treat 100% of the apertures. The results, in Table 10, show about 75% reduction in surface stain area and about 90% reduction in rewet weight compared to example 2 average.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care article comprising a nonwoven fluid permeable topsheet having a body-facing surface and an opposing backside surface, a fluid impermeable backsheet and at least one intermediate layer disposed therebetween, wherein the fluid permeable topsheet comprises apertured holes wherein at least 10% of the aperture holes include a treatment rendering the aperture holes more hydrophilic than untreated portions of the fluid permeable topsheet, and wherein the fluid permeable topsheet other than the aperture holes comprises a surface composition selected from a hydrophobic composition, a superhydrophobic composition and combinations thereof.

2. The personal care article of claim 1 wherein the treatment rendering the aperture holes more hydrophilic is a surfactant.

3. The personal care article of claim 2 wherein said surfactant is nonionic.

4. The personal care article of claim 1 wherein the treatment rendering the aperture holes more hydrophilic further comprises a viscoelastant agent selected from the group consisting of sodium citrate, dextran, cysteine, glucopan and combinations thereof.

5. The personal care article of claim 1 wherein the treatment rendering the aperture holes more hydrophilic is selected from the group consisting of polyethylene glycol laurates, polyethylene glycol lauryl ethers, and combinations thereof.

6. The personal care article of claim 1 wherein the nonwoven fluid permeable topsheet is spunbond, meltblown, coform, air-laid, bonded-carded web materials, hydroentangled (spunlace) materials, combinations thereof and the like.

7. The personal care article of claim 1 wherein the surface composition is a hydrophobic composition disposed on the body-facing surface and/or the opposing back side surface.

8. The personal care article of claim 7 wherein said hydrophobic composition is a modified perfluorinated polymer.

9. The personal care article of claim 7 wherein said hydrophobic composition is selected from the group consisting of silicones, fluorochemicals, zirconium compounds, oils, latexes, waxes, crosslinking resins, and blends thereof.

10. The personal care article of claim 9 wherein said flourochemical compounds are selected from urethanes, ureas, esters, ethers, alcohols, epoxides, allophanates, amides, amines (and salts thereof), acids (and salts thereof), carbodiimides, guanidines, oxazolidinones, isocyanurates, and biurets.

11. The personal care article of claim 1 wherein said apertured holes comprises a diameter that is larger on said body-facing surface of the nonwoven topsheet than on the opposing backside of said nonwoven topsheet.

12. The personal care article of claim 11 wherein said aperture hole diameter measured on said body-facing surface of said nonwoven topsheet is from less than about 2 mm to less than about 5 mm.

13. The personal care article of claim 12 wherein said aperture hole density measured on said body-facing surface of said nonwoven topsheet is less than about $9.3 \times 10^5$ holes per m$^2$.

14. The personal care article of claim 13 wherein said aperture hole density is from about $1.6\times10^5$ to about $3.1\times10^5$ holes/m$^2$.

15. A personal care product comprising an absorbent article wherein the absorbent article comprises a nonwoven fluid permeable topsheet, a fluid impermeable backsheet, an absorbent core and at least one intermediate layer disposed there between, wherein the fluid permeable topsheet comprises apertured holes wherein at least 10% of the aperture holes include a treatment rendering the aperture holes more hydrophilic than untreated portions of the fluid permeable topsheet, and wherein the fluid permeable topsheet other than the aperture holes comprises a surface composition selected from a hydrophobic composition, a superhydrophobic composition and combinations thereof.

16. A personal care article comprising a nonwoven fluid permeable topsheet having a body-facing surface and an opposing backside surface, a fluid impermeable backsheet and at least one intermediate layer disposed therebetween, wherein the fluid permeable topsheet comprises apertured holes wherein at least 10% of the aperture holes include a treatment rendering the aperture holes more hydrophilic than untreated portions of the fluid permeable topsheet, and wherein the fluid permeable topsheet comprises a surface composition is a superhydrophobic composition.

\* \* \* \* \*